US 8,747,841 B2

(12) United States Patent
Ahnert-Hilger et al.

(10) Patent No.: US 8,747,841 B2
(45) Date of Patent: Jun. 10, 2014

(54) POLYPEPTIDES AND USE THEREOF FOR TREATMENT OF TRAUMATIC OR DEGENERATIVE NEURONAL INJURY

(75) Inventors: Gudrun Ahnert-Hilger, Berlin (DE); Gisela Große, Berlin (DE); Fred Hofmann, Potsdam (DE); Ingo Just, Hannover (DE); Markus Höltje, Berlin (DE); Stefanie Hülsenbeck, Mainz (DE)

(73) Assignees: Ingo Inet, Hannover (DE); Gundrun Ahnart-Hilge, Berlin (DE); Markus Höltje, Berlin (DE)

( * ) Notice: Subject to any disclaimer, the term of this patent is extended or adjusted under 35 U.S.C. 154(b) by 0 days.

(21) Appl. No.: 13/262,607

(22) PCT Filed: Mar. 31, 2010

(86) PCT No.: PCT/EP2010/054335
§ 371 (c)(1),
(2), (4) Date: Nov. 25, 2011

(87) PCT Pub. No.: WO2010/112556
PCT Pub. Date: Oct. 7, 2010

(65) Prior Publication Data
US 2013/0039894 A1    Feb. 14, 2013

(30) Foreign Application Priority Data
Mar. 31, 2009    (EP) .................... 09156967

(51) Int. Cl.
*A61K 38/00*    (2006.01)
*A61K 39/08*    (2006.01)
*A01N 63/00*    (2006.01)
*C12N 9/10*    (2006.01)

(52) U.S. Cl.
CPC ........... *A61K 38/00* (2013.01); *C12Y 204/0203* (2013.01); *C12N 9/1077* (2013.01)
USPC .................... 424/94.5; 424/239.1; 424/247.1; 424/93.2; 424/93.21; 514/44 R; 514/17.7; 435/320.1

(58) Field of Classification Search
CPC . A61K 38/00; C12Y 204/0203; C12N 9/1077
See application file for complete search history.

(56) References Cited

U.S. PATENT DOCUMENTS 6,855,688 B2 *   2/2005   McKerracher ............... 424/94.5

OTHER PUBLICATIONS

Höltje et al., A 29-amino acid fragment of *Clostridium botulinum* C3 protein enhances neuronal outgrowth, connectivity, and reinnervation, FASEB Journal, vol. 23, No. 4 (2009) XP002539934.
International Search Report dated May 31, 2010.

* cited by examiner

*Primary Examiner* — Jeffrey Stucker
*Assistant Examiner* — Adam M Weidner
(74) *Attorney, Agent, or Firm* — VLP Law Group LLP; Kent H. Cheng

(57) ABSTRACT

The present invention relates to polypeptides transiently activating Ras homolog gene family member A (RhoA) GTPase, polynucleotides encoding said polypeptides and pharmaceutical compositions comprising said polypeptides or said polynucleotides. The present invention further relates to the use of said polypeptides, said polynucleotides or said pharmaceutical compositions for long-term treatment of damage of the peripheral or central nervous system.

13 Claims, 5 Drawing Sheets

Figure 3

Figure 1:
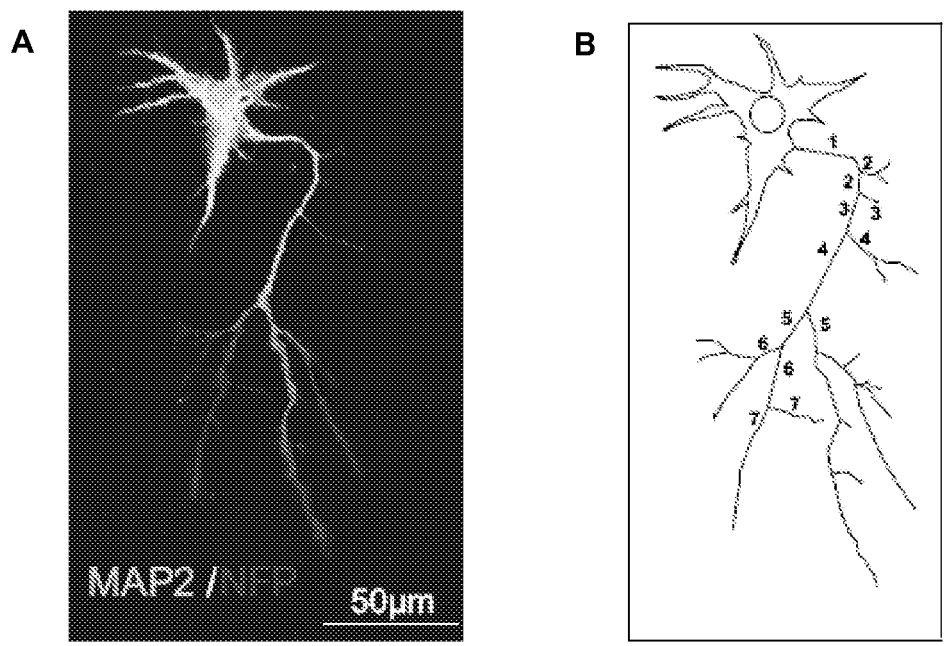

| Lane: | 1 | 2 | 3 | 4 | 5 | 6 | 7 | 8 | 9 | 10 | 11 | 12 |
|---|---|---|---|---|---|---|---|---|---|---|---|---|
| | C3$^{wt}$ | | C3$^{wt}$ +Peptide | | | C3$^{wt}$ +Peptide | | | C3$^{wt}$ +Peptide +denatur | | | ∅ Ral |
| Ral | ∅ | + | ∅ | ∅ | ∅ | + | + | + | + | + | + | |
| | | | 1 | 2 | 3 | 1 | 2 | 3 | 1 | 2 | 3 | |

Rho-[$^{32}$P]ADP ribosylation

Figure 4

C3bot$^{154-182}$   C3bot$^{156-181}$   C3bot$^{163-177}$

J774A.1

RhoA-GTP
RhoA-input 0   5   15   30   5   15   30   5   15   30   [min]

POLYPEPTIDES AND USE THEREOF FOR TREATMENT OF TRAUMATIC OR DEGENERATIVE NEURONAL INJURY

PRIORITY CLAIM

This is a U.S. national stage of application Ser. No. PCT/EP10/054335, filed on Mar. 31, 2010. Priority is claimed on the following application: EP Application No. 09156967.3 filed on Mar. 31, 2009, the content of which is incorporated here by reference.

BACKGROUND OF THE INVENTION

SEQUENCE LISTING

The instant application contains a Sequence Listing which has been submitted in ASCII format via EFS-Web and is hereby incorporated by reference in its entirety. Said ASCII copy, created on Nov. 3, 2011, is named 566123US.txt and is 8,024 bytes in size.

The present invention relates to polypeptides transiently activating Ras homolog gene family member A (RhoA) GTPase, polynucleotides encoding said polypeptides and pharmaceutical compositions comprising said polypeptides or said polynucleotides. The present invention further relates to the use of said polypeptides, said polynucleotides or said pharmaceutical compositions for long-term treatment of damage of the peripheral or central nervous system.

Formation of neurites and their differentiation into axons and dendrites requires precisely controlled changes in the cytoskeleton. During development, neurones undergo dramatic morphological changes that culminate in the differentiation of axonal and dendritic arbors. One of the first discernible steps is the generation of thin processes or neurites that elongate by the activity of growth cones at their tips.

This early developmental state is also referred to as stage 2 and lasts about 24 h. Within a few hours later, during stage 3, one of these neurites begins to grow rapidly and differentiate into an axon. During stage 4, after 3-4 days, the other neurites develop into dendrites. Once this decision is made, axons and dendrites grow and arborize more or less extensively, depending on the type of the neurone. These morphological changes require a permanent reorganization of the neuronal actin and microtubule network.

In recent years it has become clear that Rho proteins play an essential role in the differentiation of neuronal processes. Rho proteins are represented by a subfamily of small GTPases, including Rho, Rac and Cdc42 that are considered as master regulators of the cytoskeleton. However, it is not clear, which precise role Rho GTPases have during the developmentally advanced steps of elongation and arborization of axons and dendrites. In particular, it is not understood how activation or inactivation of Rho proteins influences growth and arborization of axons in comparison to that of dendrites.

Neurotrophins that regulate neuronal morphogenesis have been shown to play comparable roles in axon and dendrite development, suggesting that axonal and dendritic growth cones may share similar signal transduction machineries while extracellular effectors like semaphorin A affect axons and dendrites differently. Many of these receptor-mediated effects are linked to signals involving members of the Rho family, including Rho, Cdc42 and Rac. However, reports, especially on RhoA effects, are quite contradictionary. Growth of undifferentiated neurites (stage 2) and of those that have started to differentiate to an axon (stage 3) was promoted by either activating or inhibiting members of the Rho GTPase family. Lysophosphatidic acid (LPA), a constituent present in serum, promotes neurite retraction through a $G\alpha_{12/13}$-mediated activation of Rho. Activation of RhoA has also been shown to promote dendritic and axonal growth in rat cortical neurones cultivated in the presence of serum. Thus, RhoA appears to have variable effects on all types of processes depending on the developmental stage of the neurone and the culture conditions, especially the presence or absence of serum.

Recovery from injuries of the peripheral or the central nervous system, for instance after disruption of spinal cord motor neurones, traumatic brain injuries or damages following pathological processes, such as Morbus Parkinson, Alzheimer etc. depends on neuronal growth and regeneration.

One therapeutic approach is to influence the RhoA signalling. The Rho-inactivating C3 transferase (C3bot) from *Clostridium botulinum* is the prototype of the family of C3-like ADP-ribosyltransferases which modify GTPases of the Rho subfamily so that downstream signalling is inhibited. C3bot selectively ADP-ribosylates the Rho isoforms A, B and C, but does not influence other members of the Rho or Ras protein family. The main cellular effects of C3bot seem to be the disaggregation of the actin cytoskeleton.

However, cell entry into cultured cells is only observed in the presence of high extracellular concentrations of C3bot (μM range) and is thought to take place by pinocytosis. Thus, U.S. Pat. No. 6,855,688 B2 provides a fusion protein comprising C3bot and a transport agent facilitating the uptake of the C3bot into cells by a receptor-independent pathway through the cell membrane. Suitable transport agents are a subdomain of HIV Tat protein, a homeodomaine of antennapedia or a Histidine tag. However, due to the fact that RhoA signalling plays a pivotal role in many cell processes RhoA inactivation generated by $C_3$bot is disadvantageous in general. Further, the positive effects of RhoA activation to neuronal growth and regeneration are blocked by these substances.

WO 03/037920 A2 discloses that RhoA inactivation can be avoided, if the C3bot wild type protein (C3bot$^{wt}$) is mutated at amino acid 174. The mutated protein is ADP-ribosyltransferase inactive, but is still able to enhance neuronal growth. However, full length proteins are not optimal drug candidates due to the high immunogenicity and the poor efficacy to pass the cell membrane.

Höltje et al. disclose that a non-mutated 29 amino acid fragment of C3bot (C3bot$^{154-182}$) does not inactivate RhoA, but also exerts neurotrophic activity (A 29-amino acid fragment of *Clostridium botulinum* C3 protein enhances neuronal outgrowth, connectivity and reinnervation; The FASEB Journal, article fj. 08-116855, published online Dec. 1, 2008). The 29 amino acid fragment promotes axonal and dendritic growth as well as branching of hippocampal neurones. This fragment acts only on neuronal cells and does not influence astrocytes and microglia.

Administration of pharmaceuticals often comprises strong and uncomfortable side effects for the patient. In particular for long term administration of pharmaceuticals it is important to reduce side effects and to disturb the physiology of the patient as less as possible. Thus, pharmaceuticals are required which mimic the cell physiology, do not influence other cellular processes than the target process and show a low immunogenicity.

A further problem of pharmaceuticals or drug candidates which promote neuronal growth is that they do not influence the neurites specifically. However, different neurological diseases or damages require different therapeutics. For instance axonal growth has to be stimulated selectively following disruptures of the spinal cord and complex traumatic injuries to avoid false synaptic contacts. On the other hand dendritic branching or the formation of synaptic connections are needed to treat degenerative diseases.

SUMMARY OF THE INVENTION

It is the object of the present invention to provide active substances promoting neuronal growth and regeneration and which overcome the disadvantages of the state of the art.

It is another object of the present invention to provide neuronal growth and regeneration promoting active substances which are suitable for repeated administration and long term treatment. Thus, it is another object of the present invention to provide active substances which mimic the cellular physiology.

It is a further object of the present invention to provide active substances which promote special aspects of neuronal growth and regeneration.

The present invention relates to a polypeptide selected from the group consisting of a) the amino acid sequences of SEQ ID No: 1 to SEQ ID No: 16,
b) a polypeptide of a) modified by a substitution or mutation of at least one amino acid, wherein the identity with the polypeptide of a) is at least 70%, preferably 80%, more preferred 90%, and most preferred 95% and
c) a polypeptide comprising at least two identical amino acid sequences selected from a) or b), wherein the polypeptide of a), b) and c) transiently activates Ras homolog gene family member A (RhoA) GTPase.

The polypeptides according to the present invention are peptide fragments of the RhoA-inactivating C3 transferase from *Clostridium botulinum* (C3bot). SEQ ID No: 1, the longest fragment, is the fragment of wild type C3bot (C3bot$^{wt}$) ranging from amino acid 156 to amino acid 181 (C3bot$^{156-181}$). SEQ ID No: 2 to SEQ ID No: 16 are shorter fragments of SEQ ID No: 1. Surprisingly, the polypeptides of the invention do initially activate RhoA followed by inactivation which is in contrast to the full length wild type enzyme (C3bot$^{wt}$).

In general there is a long lasting debate on whether axonal growth will benefit from activation or inactivation of RhoA. However, under physiological conditions RhoA activation/inactivation cycles, temporally and spatially outbalanced, promote cellular processes including axon and dendritic growth. The polypeptides of the invention show axon- and dendritic promoting effects in cultivated hippocampal neurones and in the in-vitro model of entorhinal/hippocampal lesion as well as regenerative properties in the animal model. It is very advantageous that the polypeptides of the present invention act specifically on neurones and do not influence microglia cells and astrocytes so that neuronal inflammation and the formation of neuronal scars consisting of astrocyte cells is prevented. Thus, the polypeptides are useful for treating diseases or disorders marked by reduction of neuronal ramification and function, such as neurodegenerative disorders or physical or toxic damage to brain, spinal or peripheral nerve cells. That means the polypeptides of the present invention are useful for improving nerve regeneration or promoting nerve survival under a variety of neurological conditions requiring growth and branching of neuronal cells. The present invention is further useful for restoring or optimising neuronal communication, function or performance.

In an embodiment of the invention the activation of RhoA is transient so that a peak of active and signaling competent RhoA is achieved. The level of activated RhoA is 2-3 fold higher than the normal level. In another embodiment the level of activated RhoA is decreased after the initial activation peak to the normal level present in control cells and further decreased over time. A short activation peak of RhoA followed by a longer lasting inactivation mimics physiological conditions better than an uncontrolled persistent activation or knocking down of activity. In this respect the polypeptides of the present invention are superior to C3bot$^{wt}$ and the peptide fragments disclosed in the prior art, especially regarding the outcome following repeated administrations and long term treatments. It is noteworthy that the neurotrophic effects of polypeptides of the present invention represent a completely novel principle, i.e. transient RhoA activation compared to C3bot$^{wt}$ inactivating RhoA. This transient activation followed by the longer lasting inactivation promotes axon and dendrite growth under conditions resembling more the physiological RhoA activation/inactivation cycles. Thus, the polypeptides of the present invention are very advantageous for long-term treatment and reduce the physiological side effects.

It is another advantage of the polypeptides of the present invention that they do not interact with the RalA-GTPase which is also important in the regulation of neuronal and morphological differentiation and also regulates the signaling of the Rho family proteins. Due to the absence of interaction with RalA undesired side effects are further reduced.

The polypeptides of the present invention are optimal drug candidates due to small size and good effectiveness, i.e. in nanomolar concentrations. It is further advantageous that such small molecules show a low immunogenicity, an excellent pharmaceutical kinetics and are easy to produce. Due to their small size the polypeptides may also pass the blood brain barrier thus probably allowing systemic administration in the treatment of degenerative disorders. In addition, short peptides are the basis for the generation of so-called peptidomimetic compounds that are chemically synthesized having the advantage of further beneficial modification with respect to kinetics and side effects.

The polypeptides according to the invention have at least 15 consecutive amino acids of the amino acid sequence of SEQ ID No: 1 having 26 amino acids, i.e. a fragment of 15 consecutive amino acids is the shortest polypeptide of the invention. Further, the polypeptides may consist of more than 15 consecutive amino acids, in particular of 16 to 26 amino acids. If the polypeptide consists of less than 26 amino acids it can start at any position of SEQ ID No: 1, i.e. at position 1 or 1+n, wherein n is an integer between "1" and "26—the total number of amino acids of said polypeptide". Thus, the maximal number of amino acids forming the polypeptides of the present invention is 26 and the polypeptides of the present invention are fragments of SEQ ID No: 1.

According to the invention the polypeptides may be further modified by deletion addition, substitution or mutation. These polypeptides are named "modified polypeptides" or "polypeptides with modifications". Both terms as used herein relate to any polypeptide of the invention amended by a modification, in particular a deletion, addition, substitution or mutation as described below. According to the present invention the polypeptides after a deletion of (an) amino acid(s) consist of at least 15 amino acids and the maximal number of (an) amino acid(s) after an addition is 26. Deletion or addition of (an) amino acid(s) can be performed at any position within the polypeptides of the present invention. Usually the modification of the polypeptides is a point modification. A substitution is preferably made conservatively. Conservative substitutions or mutations as used herein denotes the replacement of one amino acid residue by another amino acid residue which is biologically similar. That means a cysteine/threonine or serine substitution, an acidic/acidic, a basic/basic or a hydrophobic/hydrophobic amino acid substitution, etc. is preferred. Examples of conservative substitutions include the substitution of one hydrophobic residue such as isoleucine, valine, leucine or methionine for another, or the substitution of one polar residue for another, such as the substitution of arginine for lysine, glutamic acid for aspartic acid, or glutamine for asparagine, and the like.

In another embodiment of the invention amino acids of the polypeptide are substituted by modified amino acid residues, non-standard amino acids or non-natural amino acids. Alternatively, the amino acids are modified directly. Non-standard amino acids are for example, ornithine, citrulline, taurine, selenocysteine, pyrrolysine, lanthionine, dehydroalanine, 2-aminoisobutyric acid, γ-aminobutyric acid or 3-aminopropanionic acid. Amino acids can be modified naturally or by intervention, for example, by disulfide bond formation, acetylation, amidation, carboxylation, glycosylation, hydroxylation, lipidation, methylation, phosphorylation, or any other manipulation or modification.

The polypeptides of the invention usually comprise naturally occurring amino acids but D-amino acids or amino acid mimetics coupled by peptide bonds or peptide bond mimetics may also be used. Amino acid mimetics are other than naturally occurring amino acids that conformationally mimic the amino acid for the purpose of the requisite polypeptide specificity. Suitable mimetics are known to those of ordinary skill in the art and include beta-, gamma-, delta-amino and -imino acids, cyclohexylalanine, adamantylacetic acid, etc., modifications of the amide nitrogen, the alpha-carbon, amide carbonyl or backbone modifications, etc.

According to the invention only addition, deletion, substitution or mutation of amino acids are comprised which do not alter the biological activity of the polypeptide, i.e. the modified polypeptide still activates RhoA. Preferably the polypeptides of SEQ ID No: 1 to SEQ ID No: 16 are modified by a mutation or substitution of one or more amino acids at one or more positions within the amino acid sequence.

In another embodiment of the invention the polypeptide comprises or consists of a repetition of at least two identical amino acid sequences of the invention, e.g. at least two polypeptides of at least 15 consecutive amino acids of the amino acid sequence of SEQ ID No: 1 or the modified polypeptides as described above, in particular the polypeptide comprises or consists of a repetition of at least two identical amino acid sequences of SEQ ID No: 1 to SEQ ID No: 16 or the modifications thereof. These polypeptides of the invention are also named "repetitive polypeptides". Preferably the number of identical copies of an amino acid sequence forming one polypeptide of the invention is in the range from 2 to 10, more preferred from 2 to 5 and most preferred 2 or 3.

In a preferred embodiment the repetitive amino acid sequences of the repetitive polypeptides are linked directly, for instance using a peptide bound between the at least two amino acid sequences. In a further embodiment two repetitive amino acid sequences are spaced by a pharmaceutically acceptable linker molecule. Suitable linker molecules according to the invention are for instance non-peptide spacers, such as hydrocarbon chains with 1 to 20 carbon atoms, PEG-chains with 1 to 10 PEG-groups or amino hexanoic acid and/or peptide spacer, such as a repetition of 2 to 10 glycines and/or alanines and/or an amino acid sequence comprising at least one proline. Further suitable spacer molecules are known to the skilled person.

According to the invention the repetitive polypeptides comprise only such polypeptides which still activate RhoA. Preferably the repetitive polypeptides comprise polypeptides SEQ ID No: 1 to SEQ ID No: 16.

In one embodiment the polypeptides of the invention are polypeptides consisting of 20 to 26 amino acids, preferably consisting of 23 to 26 amino acids and more preferred consisting of 26 amino acids. In a preferred embodiment of the invention the polypeptide has the amino acid sequence of any one of SEQ ID No: 1 to SEQ ID No: 10, preferably SEQ ID No: 1, or its modifications as described above. These polypeptides and their modifications according to the invention, i.e. the corresponding modified polypeptides and the corresponding repetitive polypeptides show axon- and dendritic promoting effects in cultivated hippocampal neurones and in the in-vitro model of entorhinal/hippocampal lesion as well as regenerative properties in the animal model. They induce branching of primary hippocampal neurones and increases the number of synaptic contacts so that they are useful for restoring or optimising neuronal communication, function or performance. Thus, these polypeptides of the invention show a broad neuro-regenerative activity.

In another embodiment the polypeptides of the invention are shorter polypeptides, in particular the polypeptides consisting of 15 to 19 amino acids, preferably consisting of 15 to 17 amino acids and more preferred consisting of 15 amino acids. In a preferred embodiment of the invention the polypeptide has the amino acid sequence of any one of SEQ ID No: 11 to SEQ ID No: 16, preferably SEQ ID No: 11, or its modifications as described above. In comparison to the longer polypeptides of the invention these shorter polypeptides and their modifications according to the invention, i.e. the corresponding modified polypeptides and the corresponding repetitive polypeptides show a further reduced immunogenicity, further improved pharmaceutical kinetics and a better passage of blood brain barrier. Advantageously, said short polypeptides of the invention can also be used as basis to generate peptidomimetic substances which do not show any immunogenicity, which do cross the blood-brain barrier and which penetrate into neuronal tissues.

Surprisingly, these short polypeptides show additional effects which are related to one special aspect of neuronal growth and regeneration. They selectively act on axons, but does not influence dendrites thereby avoiding the formation of undesired synaptic contacts, i.e. when nearby axons will represent a concurrence for farer away axons due to the released axonotrophic factors from the dendritic site. Such conditions arise from traumatic brain injuries and represent less perfect repair mechanism. These "false" connections may favour, for instance epileptic seizures or other adverse effects. Due to its selective axonotrophic effects the polypeptides consisting of 15 to 19 amino acids, preferably consisting of 15 to 17 amino acid, especially the polypeptides consisting of an amino acid sequence of any one of SEQ ID No: 11 to SEQ ID No: 16, more preferred consisting of 15 amino acids and most preferred consisting of SEQ ID No: 11 may represent the drug of choice when regeneration in a complex network is demanded.

Special axonotropic effect is also needed when the spinal cord is injured and the long axons of afferent and efferent neurones are damaged. For restoring the function of the body parts affected it is important that axon regeneration is selectively accelerated.

An especially preferred short polypeptide of the invention is the polypeptide of the amino acid sequence of SEQ ID No: 11 consisting of 15 amino acids and its modifications and repetitions according to the invention. The polypeptide of SEQ ID No: 11 is the fragment starting at position 8 of SEQ ID No: 1, i.e the polypeptide of SEQ ID No: 11 is also a fragment of C3bot$^{wt}$ ranging from amino acid 163 to amino acid 177 (C3bot$^{163-177}$).

Surprisingly, the polypeptides of the invention easily pass the cell membrane as well as the blood brain barrier and are already effective at nanomolar concentrations. However, to further improve uptake into the cells in order to reduce pharmaceutically required doses the polypeptides can be further modified. The polypeptides of the invention can be bound to or encapsulated into a transport agent facilitating the uptake of the polypeptide into mammal cells in one embodiment of the invention. In another embodiment of the invention the transport agent further facilitates the transport through the blood brain barrier.

According to the invention the term "binding" includes all variants of binding known to the skilled person and the term "encapsulating" includes all forms of shielding or packing into biologic or synthetic pharmaceutically acceptable envelopes or capsules.

Suitable forms of binding comprise for instance covalent binding, ionic binding, hydrophobic interaction, such as Vander-Waals interaction, electrostatic interaction, dipol-dipol interaction, formation of a hydrogen bridge or complexing. Covalent binding according to the invention can be performed by any binding known to the skilled person. According to the invention peptide binding is preferred. Suitable substances which are covalently bound to the polypeptides of the present invention are His-tags, haemagglutinin (HA)-tags or parts of viral proteins responsible for uptake into cells or ligand molecules to use receptor mediated uptake, such as glucose.

Suitable biologic or synthetic pharmaceutically active capsules or envelopes according to the invention are viral capsides, viroidic capsules, resealed erythrocytes, micelles, such as liposomes, niosomes, nanoparticles, for instance solid lipid nanoparticles, poly(lactic-co-glycolic) acid (PGLA)-microspheres, bioabsorbable matrices, such as hydrocolloid capsules, hydroxypropyl-methylcellulose capsules, charged or non-charged polymernanoparticles (polymersomes), for instance consisting of amphiphilic block-copolymers, or poly-ethylene glycol containing polymers or soluble macromolecules, such as cyclodextrins, in particular alpha-, beta- and gamma-cyclodextrins.

Suitable liposomes are for instance multivesicular liposomes (MVL), multilamellar liposomes (also known as multilamellar vesicles or MLV), unilamellar liposomes, including small unilamellar liposomes (also known as unilamellar vesicles or SUV) and large unilamellar liposomes (also known as large unilamellar vesicles or LUV). The composition of the synthetic liposomes is usually a combination of phospholipids, usually in combination with steroids, especially cholesterol. Other phospholipids or other lipids may also be used. Examples of lipids useful in synthetic liposome production include phosphatidylglycerols, phosphatidylcholines, phosphatidylserines, phosphatidylethanolamines, sphingolipids, cerebrosides and gangliosides. Preferably, phospholipids including egg phosphatidylcholine, dipalmitoylphosphatidylcholine, distearoylphosphatidylcholine, dioleoylphosphatidylcholine, dipalmitoylphosphatidylglycerol, and dioleoylphosphatidylglycerol are used.

Niosomes are unilammelar, bilammellar or multilammelar vesicles formed of non-ionic surface active agents, for instance from the alkyl or dialkyl polyglycerol ether class or cholesterol in aqueous solutions. Niosomes are similar to liposomes in functionality.

Suitable bioabsorbable matrices preferably comprise one or more macromolecules selected from the group consisting of collagen, elastin, fibronectin, vitronectin, laminin, polyglycolic acid, hyaluronic acid, chondroitin sulfate, dermatan sulfate, heparin sulfate, heparin, fibrin, cellulose, gelatin, polylysine, echinonectin, entactin, thrombospondin, uvomorulin, biglycan, decorin and dextran.

Capsules or envelopes according to the present invention can be further modified. For instance PEG-modification at the surface of synthetic envelopes can be used to decrease the immunogenicity of the capsules or addition of apolipoprotein E (ApoE) can be used to facilitate the uptake into the brain passing the blood brain barrier.

According to the invention addition of His-tags, haemagglutinin (HA)-tags or glucose-tags or encapsulation into liposomes, niosomes, polymersomes, bioabsorbable matrices, cyclodextrines or biological envelopes is preferred.

Furthermore, the heavy chain of clostridial neurotoxins can be applied to specifically deliver the polypeptides into neurones (Bade S et al., Botulinum neurotoxin type D enables cytosolic delivery of enzymatically active cargo proteins to neurones via unfolded translocation intermediates. J. Neurochem. 2004 December; 91(6):1461-72.)

In a preferred embodiment of the invention the polypeptides are produced synthetically. Peptide synthesis techniques are known to the skilled person. Suitable examples are liquid-phase synthesis, for instance using carbodiimides as activating agents, solid-phase synthesis techniques, such as t-Boc solid phase synthesis, Fmoc solid-phase synthesis or BOP solid-phase synthesis, or microwave assisted peptide synthesis.

The polypeptides can also be produced using bioengineering techniques. Thus, in a further object the present invention provides a polynucleotide consisting of a nucleotide sequence encoding the polypeptides of the present invention. As used herein the term "polypeptide" comprises the polypeptides consisting of at least 15 consecutive amino acids of the amino acid sequence of SEQ ID No: 1, wherein the maximal number of amino acids is 26 as well as their modified polypeptides and repetitive polypeptides. Preferably the term "polypeptide" comprises the polypeptides consisting of the amino acid sequence of SEQ ID No: 1 to SEQ ID No: 16.

The term "polynucleotide" is used to mean a polymeric form of nucleotides of variable length, which contains deoxyribonucleotides, ribonucleotides, and/or their analogs. According to the invention the term polynucleotide encompasses both the double-stranded form and each of two complementary single-stranded forms known or predicted to make up the double stranded form as well as triple-helical molecules comprising at least one single stranded polynucleotide encoding the polypeptide of the present invention. According to the invention the polynucleotide is preferably genomic DNA, cDNA or RNA.

In another object of the present invention a vector comprising the polynucleotide encoding the polypeptide of the present invention is provided. The invention further relates to a host cell transfected with said vector. The invention further relates to the host cells comprising the polypeptide, the polynucleotide and/or the vector of the invention.

As used herein singular and plural forms of "polypeptide", "polynucleotide", "vector" or "host cell" are used interchangeable and mean one or several polypeptide(s), polynucleotide(s), vector(s) or host cell(s) of the invention.

The present invention also provides a method of producing a polypeptide of the invention biotechnologically comprising the steps of introducing a polynucleotide encoding the polypeptide of the invention or a vector comprising said polynucleotide into a host cell, culturing said host cell under conditions suitable for expression of said polypeptide and recovering said polypeptide of the invention from the host cell.

A large number of vectors, including plasmid and viral vectors, have been described for expression in a variety of eukaryotic and prokaryotic hosts. Advantageously, vectors will often include a promotor operably linked to the polypeptide-encoding portion, one or more replication systems for cloning or expression and one or more markers for selection in the host, e.g. antibiotic resistance. Suitable vectors are known to the skilled person. A preferred vector system according to the invention is the plasmid pGEX-2T. The inserted polynucleotide may be synthetically synthesized, isolated from natural sources, prepared as hybrids, etc.

Suitable host cells may be transformed, transfected and/or infected by any suitable method known to the skilled person, for instance electroporation, $CaCl_2$-mediated DNA uptake, viral infection, microinjection or other methods. Appropriate host cells include bacteria, archebacteria, fungi, especially yeast and *Neurospora*, plant cells and animal cells, especially mammalian cells. Of particular interest are *Escherichia coli* (*E. coli*), in particular *E. coli* TG1, *Bacillus subtilis, Bacillus megaterium, Saccharomyces cerevisiae*, SF9 cells, C129 cells, 293 cells, CHO, COS, HeLa cells or immortalized mammalian myeloid and lymphoid cell lines. Preferred expression systems include COS-7, HEK-293, BHK, CHO, CHOp38, BON, PC12, SHSY, C6, F98, TM4, CV1, VERO-76, HELA, MDCK, BRL 3A, W138, Hep G2, MMT 060562, TR1 cells, and baculovirus systems. Preferred replication systems include M13, ColE1, SV40, baculovirus, lambda, adenovirus, AAV, BPV, etc. A large number of transcription, initiation and termination regulatory regions have been isolated and shown to be effective in the transcription and translation of heterologous proteins in various hosts. Examples of these regions, methods of isolation, manner of manipulation, etc. are known in the art. In another embodiment of the invention stably transformed host cells are established. Methods of producing stably transformed host cells depend on the special cell type and are known to the skilled person.

The polypeptides of the invention may be isolated or purified in a variety of ways known to those skilled in the art depending on what other components are present in the sample and to what, if anything, the polypeptide is covalently linked. Purification methods include electrophoretic, molecular, immunological and chromatographic techniques, especially affinity chromatography and RP-HPLC in the case of peptides.

In a preferred embodiment of the invention the polypeptides are expressed as recombinant GST-fusion proteins in suitable bacteria such as *E. coli* TG1. GST-fusion polypeptides were purified by column chromatography and the purified polypeptides were cleavage from the GST-tag and eluted from the column.

In a further object the present invention provides a pharmaceutical composition comprising a pharmaceutically effective amount of the polypeptide of the invention and/or the polynucleotide encoding said polypeptide, the vector comprising said polynucleotide and/or the host cell comprising said vector and pharmaceutically acceptable excipients. The present invention also relates to a pharmaceutical composition comprising an effective amount of the polypeptide of the invention and/or the polynucleotide encoding said polypeptide, the vector comprising said polynucleotide and/or the host cell comprising said polypeptide, said polynucleotide and/or said vector and pharmaceutically acceptable excipients.

According to the invention the polypeptide of the invention, the polynucleotide encoding said polypeptide, the vector comprising said polynucleotide and/or the cell comprising said polypeptide, said polynucleotide and/or said vector are also termed the "active substance" of the pharmaceutical compositions of the invention. As used herein singular and plural forms of "active substance" or "pharmaceutical composition" are used interchangeable and mean one or several active substance(s) or pharmaceutical composition(s) of the invention.

The active substance of the invention can also be formulated into the pharmaceutical composition of the invention as a pharmaceutically acceptable salt. Pharmaceutically acceptable salts include the acid addition salts (formed with the free amino groups of the polypeptide) that are formed with inorganic acids such as, for example, hydrochloric acid or phosphoric acid, or organic acids, such as e.g. acetic acid, tartaric acid, mandelic acid and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

The term "excipient" is used herein to describe any ingredient other than the active substance of the invention. The choice of excipient will to a large extent depend on the particular mode of administration. Excipients can be for instance suitable carriers, retardants, boosters, prolonging substances, adjuvants, stabilizers, binders, emulsifiers, surface active agents, penetration enhancers, suspending agents, disintegrants, buffers, salts, carbohydrates, diluents, solvents, dispersion media, fillers, lubricants, propellants, preservatives, flavours or mixtures thereof.

The active substance and/or the pharmaceutical composition of the invention may be administered in any one of the following administration forms, for instance enteral, such as oral or rectal and/or parenteral, such as transdermal, transmucosal or via injections and/or directly during a surgical intervention as a solution or as a deposit preferably incorporated into a biodegradable, such as an absorbable hydrocolloid matrix.

Oral administration may involve swallowing, so that the composition enters the gastrointestinal tract, or buccal or sublingual administration may be employed by which the composition enters the blood stream directly from the mouth. Formulations suitable for oral administration include: solid formulations such as tablets, capsules containing particulates, liquids, or powders, lozenges (including liquid-filled), and chews, multi- and nano-particulates, gels, solid solutions, liposomes, films, ovules, sprays and liquid formulations.

Liquid formulations include suspensions, solutions, syrups and elixirs. Such formulations may be employed as fillers in soft or hard capsules and typically comprise a carrier, for example, water, ethanol, glycerin, polyethylene glycol, propylene glycol, methylcellulose, dextrose or a suitable oil, such as a vegetable oil e.g. olive oil or organic esters, such as ethyl oleate, one or more emulsifying agents and/or suspending agents and one or more buffers. Liquid formulations may also be prepared by the reconstitution of a solid, for example, from a sachet.

The pharmaceutical composition of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the active substance of the invention may make up from 1 weight % to 80 weight % of the dosage form, more typically from 5 weight % to 60 weight % of the dosage form. In addition to the active substance of the invention, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colourants, flavouring agents, preservatives and taste-masking agents.

Exemplary tablets contain up to about 80 weight % the active substance of the invention, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in Pharmaceutical Dosage Forms: Tablets, Vol. 1, by H. Lieberman and L. Lachman (Marcel Dekker, New York, 1980).

Consumable oral films for human use are typically pliable water-soluble or water-swellable thin film dosage forms which may be rapidly dissolving or mucoadhesive and typically comprise the active substance, a film-forming polymer, a binder, a solvent, a humectant, a plasticiser, a stabiliser or emulsifier, a viscosity-modifying agent and a solvent. Some components of the formulation may perform more than one function.

The pharmaceutical composition may be water-soluble or insoluble. A water-soluble composition typically comprises from 1 weight % to 80 weight %, more typically from 20 weight % to 50 weight %, of the solutes. Less soluble compositions may comprise a greater proportion of the composition, typically up to 88 weight % of the solutes. Alternatively, the pharmaceutical composition may be in the form of multiparticulate beads.

The film-forming polymer may be selected from natural polysaccharides, proteins, or synthetic hydrocolloids and is typically present in the range from 0.01 to 99 weight %, more typically in the range 30 to 80 weight %.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Pharmaceutical Technology On-line, 25(2), 1-14, by Verma et al (2001). The use of chewing gum to achieve controlled release is described in WO 00/35298.

The active substance of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, perineural, perilesional, intramuscular and subcutaneous. Perilesional, perineural, intracranial or intrathecal administration, for instance into the cerebrospinal fluid, a cerebral ventricle, the lumbar area or the cisterna magna is preferred. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of the pharmaceutical composition of the invention used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active substance. Examples of such formulations include drug-coated stents and PGLA microspheres.

The pharmaceutical composition of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated [see for example, J Pharm Sci, 88 (10), 955-958 by Finnin and Morgan (October 1999)].

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

The pharmaceutical composition of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the active substance of the invention comprising, for example, ethanol, aqueous ethanol, or a suitable alternative agent for dispersing, solubilising, or extending release of the active substance, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the active substance of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the active substance of the invention per actuation and the actuation volume may vary from 1 µl to 100 µl. A typical formulation may comprise an active substance of the invention, propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 0.001 mg to 10 mg of the pharmaceutical composition of the invention. The overall daily dose will typically be in the range 0.001 mg to 40 mg of the active substance which may be administered in a single dose or, more usually, as divided doses throughout the day. The pharmaceutical composition of the invention may be particularly suitable for an administration by inhalation.

The pharmaceutical composition of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

The pharmaceutical composition of the invention may also be administered directly and locally during a surgical intervention at the central or peripheral nervous system, preferably at the brain or at the spinal cord. The pharmaceutical composition may be administered as a solution or as a deposit, such as a gel-foam or a biodegradable, for instance an absorbable hydrocolloid matrix. Examples for suitable biodegradables are given above. In constructing for instance a hydrocolloid matrix, it may be useful for the matrix to further include a substructure for stability. Suitable substructures include freeze dried sponges, powders, films, flaked or broken films, aggregates, microspheres, fibres, fibre bundles, or a combination thereof. In addition, the matrix may be attached to a solid support for administration purposes. Suitable supports depend upon the specific use and can include a prosthetic device, a porous tissue culture insert, an implant, a suture, and the like. In a preferred embodiment of the invention the pharmaceutical composition is administered directly and locally, for instance using a gel-foam.

Formulations for direct local administration may be formulated to be immediate and/or modified release. Modified release formulations include delayed-, sustained-, pulsed-, controlled-, targeted, or programmed release.

According to the invention the term "modified release" means the continual delivery of the active substance of the pharmaceutical compositions of the invention to a subject for at least one, two, three, four or more weeks, preferably 1 to 30 days, after administration. As used herein, the term "subject" is intended to include animals susceptible to injuries of the central or peripheral nervous system and degenerative diseases. Mammals and in particular humans are preferred.

In a preferred embodiment the pharmaceutical composition of the invention comprises an effective amount of the active substance of the invention. The term "effective amount" denotes an amount of the active substance of the invention having a prophylactically or therapeutically relevant effect on a disease or pathological condition. A prophylactic effect prevents the outbreak of a disease. A therapeutic effect relieves to some extent one or more symptoms of a disease or returns to normal either partially or completely one or more physiological or biochemical parameters associated with or causative for the disease or pathological condition. The respective amount for administering the active substance of the invention is sufficiently high in order to achieve the desired prophylactic or therapeutic effect and should not be so large as to cause adverse side effects. It will be understood by the skilled person that the specific dose level, frequency and period of administration to any particular mammal will depend upon a variety of factors including the activity of the specific components employed, the age, body weight, general health, sex, diet, time of administration, route of administration, drug combination, and the severity of the specific therapy. A therapeutically effective amount of slow release formulation refers to the total dosage released during the total time period of administration. Using well-known means and methods, the exact amount can be determined by one of skill in the art as a matter of routine experimentation.

For administration to human patients, the pharmaceutically effective amount of the active substance in the pharmaceutical composition is typically an amount such that when it is administered in a physiologically tolerable composition, it is sufficient to achieve a plasma or local concentration of from about 0.001 µM to 10 mM, preferably from about 0.01 µM to 1 mM, more preferred from about 0.1 µM to 100 µM.

According to the invention it is very advantageous to administer the pharmaceutical composition of the invention locally at the site of lesion. Such local administration is typically by topical or local administration of a liquid composition, a gel-foam or a biodegradable matrix containing the active substance in a concentration in the range of 1 to 1000 µM, preferably about 5 to 500 µM, more preferred 10 to 100 µM, and most preferred at about 50 µM.

Alternatively, the dosage of the active substance of the invention can be metered in terms of the body weight of the patient to be treated. The following dosages are based on an average human subject having a weight of about 70 kg. The physician will readily be able to determine doses for subjects whose weight falls outside this range, such as infants and the elderly. Typical total daily doses are in the range of 0.001 mg to 5000 mg, preferably in the range of 0.001 mg to 100 mg and more preferred in the range of 0.001 mg to 50 mg.

The total daily dose depends of course, on the mode of administration. For example, an intravenous daily dose may only require from 0.001 mg to 40 mg, whereas an oral daily dose may require from 0.001 mg to 5000 mg. The total daily dose may be administered in single or divided doses and may, at the physician's discretion, fall outside of the typical range given herein.

In a further object the present invention uses the polypeptide of the invention, the polynucleotide encoding said polypeptide, the vector comprising said polynucleotide, the cell comprising said polypeptide, said polynucleotide and/or said vector and/or the pharmaceutical composition comprising said polypeptide, said polynucleotide, said vector and/or said cell to promote neural growth and/or neural regeneration and/or to transiently activate RhoA GTPase in-vitro.

As used herein, the terms "neuronal growth" or "neuronal outgrowth" refer to the process by which processes or neurites grow out of a neurone. The outgrowth can result in a totally new axon and/or dendrite(s) and/or the repair of a partially damaged axon and/or dendrite(s). Outgrowth is typically evidenced by extension of a neuronal process of at least 2-5 cell diameters in length. The term "neurones of the central nervous system" is intended to include the neurones of the brain and the spinal cord, the term neurones of the peripheral nervous system is intended to include neurones of spinal ganglia and ganglia of the vegetative nervous system.

The present invention relates further to a method of treating central or peripheral neurones in-vitro, wherein the peripheral or central neurones are brought into contact with an effective amount of the active substance of the invention. Thereby the axonal and/or dendritic outgrowth is modulated, preferably promoted and/or accelerated. The active substances of the invention can be further used to induce an expansion and/or differentiation of neuronal stem cells derived form both embryonic and adult stem cells in-vitro. The active substances may be applied at any state of differentiation and promotes and/or accelerates the process of differentiation.

Accordingly, neurones, neuronal cells and/or neuronal stem cells are isolated from a subject and grown in vitro, using techniques well known in the art (e.g. A 29-amino acid fragment of *Clostridium botulinum* C3 protein enhances neuronal outgrowth, connectivity and reinnervation; The FASEB Journal, article fj. 08-116855, published online Dec. 1, 2008). In a preferred embodiment the cultured cells are contacted with the active substance of the invention by adding the active substance to the cell culture medium or by immobilizing the active substance on a substrate and culturing the neuronal cells on top of the coated substrates. In-vitro treated neurones or in-vitro differentiated neuronal stem cells can be used as search tools for understanding for example neuronal regeneration, in particular neuronal growth, branching and survival.

The in-vitro treatment of neuronal cells with the active substances of the present invention can be further used for identifying booster and/or auxiliary substances which improve the neurotrophic effect of the active substance. If the treated cells are re-administered to the subject for treating neuronal damages, the in-vitro treatment of neuronal cells with the active substances of the invention is a part of cell based therapies.

The composition for in-vitro cell treatment of the present invention comprises at least an effective amount of the active substance of the invention and optionally a physiologically acceptable carrier. Any physiologically acceptable carrier can be used as long as it is generally used to culture and grow cells, such as a culture medium or a buffer, e.g. phosphate-buffered saline (PBS).

Advantageously the active substances of the invention are effective in in-vitro use at very low, i.e. nanomolar concentrations. An effective amount of the active substances of the invention for in-vitro application is in the range of 0.1 to 100 nM, preferably in the range of 1 to 80 nM, more preferred in the range of 10 to 60 nM and most preferred at about 50 nM.

The present invention further relates to the specific use of the polypeptides of the invention consisting of 15 to 19 amino acids, preferably consisting of 15 to 17 amino acids and more preferred consisting of 15 amino acids, the polynucleotides encoding said polypeptides, the vectors comprising said polynucleotides, the cells comprising said polypeptides, said polynucleotides and/or said vectors, and/or the pharmaceutical composition comprising said polypeptide, said polynucleotide, said vector and/or said cell for in-vitro axonal stimulation. In a preferred embodiment of the invention the polypeptide having the amino acid sequence of any one of SEQ ID No: 11 to SEQ ID No: 16, preferably having the amino acid sequence of SEQ ID No: 11, or its modifications according to the invention, the polynucleotide encoding said polypeptide, the vector comprising said polynucleotide, the cell comprising said polypeptide, said polynucleotide and/or said vector and/or the pharmaceutical composition comprising said polypeptide, said polynucleotide, said vector and/or said cell are used to promote axonal growth and/or axonal regeneration in-vitro without promoting dendritic growth.

In a further object the present invention provides the polypeptide of the invention, the polynucleotide encoding said polypeptide, the vector comprising said polynucleotide, the cell comprising said polypeptide, said polynucleotide and/or said vector and/or the pharmaceutical composition comprising said polypeptide, said polynucleotide, said vector and/or said cell for prophylactic and/or therapeutic long-term treatment of a damage of the central or peripheral nervous system.

The present invention further relates to the use of the polypeptide of the invention, the polynucleotide encoding said polypeptide, the vector comprising said polynucleotide and/or the cell comprising said polypeptide, said polynucleotide and/or said vector for the preparation of a pharmaceutical composition for prophylactic and/or therapeutic long-term treatment of a damage of the central or peripheral nervous system. In a preferred embodiment the pharmaceutical composition of the invention is administered continuously and/or repeatedly over a longer period of time.

The present invention further relates to the use of the polypeptide of the invention, the polynucleotide encoding said polypeptide, the vector comprising said polynucleotide and/or the cell comprising said polypeptide, said polynucleotide and/or said vector for preparation of a pharmaceutical composition for selective prophylactic and/or therapeutic long-term treatment of axonal damage.

In a further object the present invention provides the polypeptide of the invention, preferably the polypeptide consisting of the amino acid sequence of any one of SEQ ID No: 11 to SEQ ID No: 16, and most preferred the polypeptide of SEQ ID No: 11, or its modifications according to the invention for selective prophylactic or therapeutic long-term treatment of axonal damage. In a further object the present invention provides the polynucleotide encoding the polypeptide of the invention, preferably the polynucleotide encoding the polypeptide consisting of the amino acid sequence of any one of SEQ ID No: 11 to SEQ ID No: 16, most preferred the polypeptide of SEQ ID No: 11, the vector comprising said polynucleotide, the cell comprising said polypeptide, said polynucleotide and/or said vector for selective prophylactic or therapeutic long-term treatment of axonal damage. In a further object the present invention provides a pharmaceutical composition comprising said polypeptide, said polynucleotide, said vector and/or said cell, preferably comprising the polypeptide consisting of the amino acid sequence of any one of SEQ ID No: 11 to SEQ ID No: 16, most preferred the polypeptide of SEQ ID No: 11, the polynucleotide comprising said polypeptide, the vector comprising said polynucleotide, the cell comprising said polypeptide, said polynucleotide and/or said vector for selective prophylactic or therapeutic long-term treatment of axonal damage.

In a preferred embodiment of this specific purpose the shorter polypeptides consisting of 15 to 19 amino acids, preferably consisting of 15 to 17 amino acids, in particular the polypeptides consisting any one of the amino acid sequences of SEQ ID NO: 11 to SEQ ID No: 16, and most preferred consisting of the amino acids of SEQ ID NO: 11, the polynucleotides encoding said polypeptides, the vectors comprising said polynucleotides, the cells comprising said polypeptides, said polynucleotides and/or said vectors and/or the pharmaceutical compositions comprising said polypeptides, said polynucleotides, said vectors and/or said cells are used. Most preferred is the polypeptide of amino acid sequence of SEQ ID No: 11, polynucleotides encoding said polypeptide, the vectors comprising said polynucleotides, the cells comprising said polypeptide, said polynucleotides and/or said vectors and/or the pharmaceutical compositions comprising said polypeptide, said polynucleotides, said vectors and/or said cells for selective prophylactic or therapeutic long-term treatment of axonal damage.

According to the invention the term "damage" include any effect which directly or indirectly affects the normal functioning of the central nervous system or the peripheral nervous system. Damage according to the invention is due to traumatic injury, such as injury to retinal ganglion cells, to cells of the spinal cord or to cells of the brain, surgical lesions, a stroke or a cerebral aneurism. Traumatic spinal cord injuries comprise monoplegia, diplegia, paraplegia, hemiplegia and quadriplegia. According to the invention the damage may also be due to a neuroproliferative disorder, a neuropathic pain syndrome, a degenerative disorder, bacterial or viral infection, toxin exposure or malignant diseases. In a preferred embodiment of the invention the damage has occurred to the spinal cord.

According to the invention traumatic brain injuries include all the conditions in which, a traumatic blow to the head causes damage to the brain, often without penetrating the skull. Usually, the initial trauma can result in expanding hematoma, subarachnoid hemorrhage, cerebral edema, raised intracranial pressure, and cerebral hypoxia, which can, in turn, lead to severe secondary events due to low cerebral blood flow. The term "stroke" is intended to include sudden diminution or loss of consciousness, sensation, and voluntary motion caused by rapture or obstruction (e.g. by a blood clot) of an artery of the brain. Further reasons and symptoms of traumatic brain injuries or strokes are known to the skilled person.

The present invention also provides methods for stimulating the outgrowth of central and/or peripheral nervous system neurones following an injury. Thus, the present invention also relates to a method for prophylactic or therapeutic long-term treatment of diseases, disorders and injuries related to damages to the central and/or peripheral nervous system. Said method involves at least administering to a subject an active substance and/or pharmaceutical composition of the invention.

The present invention relates to a method for prophylactic or therapeutic long-term treatment of a damage of the central and/or peripheral nervous system in a mammal comprising administering to a mammal in need of this treatment an effective amount of at least one polypeptide of the invention, the polynucleotide encoding said polypeptide, the vector comprising said polynucleotide, the cell comprising said polypeptide, said polynucleotide and/or said vector and/or a pharmaceutical composition comprising said polypeptide, said polynucleotide, said vector or said cell.

Exemplary diseases, disorders and injuries that may be treated by administering the active substances and/or pharmaceutical compositions of the invention include, but are not limited to, cerebral injury, spinal cord injury, stroke, demyelinating diseases, e.g., multiple sclerosis, monophasic demyelination, encephalomyelitis, multifocal leukoencephalopathy, panencephalitis, Marchiafava-Bignami disease, Spongy degeneration, Alexander's disease, Canavan's disease, metachromatic leukodystrophy, and Krabbe's disease.

The degenerative disorder that may be treated with the active substances and/or the pharmaceutical compositions of the present invention comprises Parkinson's disease, amyotrophic lateral sclerosis, Alzheimer's disease, diffuse cerebral cortical atrophy, Lewy-body dementia, Pick disease, mesolimbocortical dementia, thalamic degeneration, Huntington chorea, cortical-striatal-spinal degeneration, cortical-basal ganglionic degeneration, cerebrocerebellar degeneration, familial dementia with spastic paraparesis, polyglucosan body disease, Shy-Drager syndrome, olivopontocerebellar atrophy, progressive supranuclear palsy, dystonia musculorum deformans, Hallervorden-Spatz disease, Meige syndrome, familial tremors, Gilles de la Tourette syndrome, acanthocytic chorea, Friedreich ataxia, Holmes familial cortical cerebellar atrophy, Gerstmann-Straussler-Scheinker disease, progressive spinal muscular atrophy, progressive balbar palsy, primary lateral sclerosis, hereditary muscular atrophy, spastic paraplegia, peroneal muscular atrophy, hypertrophic interstitial polyneuropathy, heredopathia atactica polyneuritiformis, optic neuropathy, and/or ophthalmoplegia.

The terms "treatment" and "therapeutically," as used herein, refer to the act of treating, as "treating" is defined below. As used herein, the term "treating" refers to reversing, alleviating and/or inhibiting the progress of a disease, disorder and/or condition, and/or one or more symptoms of such disease, disorder and/or condition, to which such term applies. As used herein, "treating" may also refer to decreasing the probability and/or incidence of the occurrence of a disease, disorder and/or condition in a mammal as compared to an untreated control population, or as compared to the same mammal prior to treatment. For example, as used herein, "treating" may refer to preventing a disease, disorder and/or condition, and may include delaying and/or preventing the onset of a disease, disorder and/or condition, and/or delaying and/or preventing the symptoms associated with a disease, disorder and/or condition. As used herein, "treating" may also refer to reducing the severity of a disease, disorder and/or condition and/or symptoms associated with such disease, disorder and/or condition prior to a mammal's affliction with the disease, disorder and/or condition. Such prevention and/or reduction of the severity of a disease, disorder and/or condition prior to affliction relates to the administration of the composition of the present invention, as described herein, to a subject that is not at the time of administration afflicted with the disease, disorder and/or condition. As used herein "treating" may also refer to preventing the recurrence of a disease, disorder and/or condition and/or of one or more symptoms associated with such disease, disorder and/or condition.

Treating and/or contacting of the injured nerve with the active substances and/or pharmaceutical compositions of the invention soon after injury is particularly important for accelerating the rate and extent of recovery. Thus the invention contemplates a method of treating damages of the central and/or peripheral nervous system comprising administering locally to the subject a physiologically tolerable and effective amount of the active substances and/or pharmaceutical composition of the invention as soon as possible after the damage occurred.

For treatment according to the invention the active substances and/or the pharmaceutical compositions of the invention are administered at a daily dose per treatment cycle of not more than 20 mg/kg, preferably of not more than 10 mg/kg, more preferably selected from the range of 1 μg/kg to 5 mg/kg body weight.

In a further object the present invention provides a kit comprising the polypeptide of the invention, the polynucleotide encoding said polypeptide, the vector comprising said polynucleotide, the host cell comprising said polypeptide, said polynucleotide and/or said vector and/or the pharmaceutical composition of the invention comprising said polypeptide, said polynucleotide, said vector and/or said cell optionally with written information, instructions for use and/or means for administration. The kit may be used by the medical practitioner or by the subject to be treated directly. Thus, the written information and direction for use is directed to a skilled person or a medical layperson and the information is adopted accordingly. Means for administration are adopted to the administration form and the texture of the active substances and/or the pharmaceutical composition.

DESCRIPTION OF THE FIGURES

FIG. 1A shows a confocal imaging of a fixed hippocampal neuronal cell immunostained for an axonal and a dendritic marker, respectively. FIG. 1B shows a simplified drawing of FIG. 1A used for segment order analysis.

FIG. 2 shows the results of ADP-ribosylation of RhoA by $C3bot^{wt}$ and C3bot-derived peptide fragments $C3bot^{154-182}$, and $C3bot^{163-177}$.

FIG. 3 shows that RalA interacts with $C3bot^{wt}$, but does not interact with the C3bot peptide fragments $C3bot^{156-181}$ and $C3bot^{163-177}$.

FIG. 4 shows that the C3bot peptide fragments $C3bot^{156-181}$ and $C3bot^{163-177}$ transiently activate RhoA-GTPase.

FIG. 5 shows the effects of C3bot peptide fragments on process growth of hippocampal neurones in-vitro.

FIG. 6: shows that $C3bot^{156-181}$ but not $C3bot^{163-177}$ affects the number of synaptophysin expressing synaptic terminals in hippocampal neurons.

FIG. 7 shows the effects of C3bot peptide fragments $C3bot^{156-181}$ and $C3bot^{154-182}$ on behavioural recovery after spinal cord injury in-vivo.

DETAILED DESCRIPTION OF THE PRESENTLY PREFERRED EMBODIMENTS

These and further advantages of the present invention will become apparent to the skilled person by reading and understanding the following examples which are intended to illustrate, but not to limit the present invention.

EXAMPLE 1

Expression and Purification of Recombinant C3Bot Protein

The gene of *Clostridium botulinum* C3 wild type ($C3bot^{wt}$) (SEQ ID No: 17) was expressed as a recombinant GST-fusion protein in *E. coli* TG1 (ATCC) by cloning the respective DNA fragment into the plasmid pGEX-2T (ATCC).

Bacteria were grown at 37° C. in 1 L of Luria-Bertani (LB) medium containing 100 μg/ml ampicillin to an optical density (595 nm) of 0.7. IPTG (isopropyl-1-thio-D-galactopyranoside) was added to a final concentration of 0.2 mM, and the cultures were incubated at 37° C. for another 3 h. Bacteria were sedimented at 7700 g (15 min, 4° C.) and resuspended in 20 ml lysis buffer (500 mM NaCl and 50 mM NaPP, pH 7.2) complemented with protease inhibitor cocktail, EDTA free (Roche, Mannheim, Germany). Bacteria were lysed by means of a French pressure cell press System (SIM Aminco Spectronic Instruments, Rochester, N.Y., USA), and the bacterial debris was sedimented at 12,000 g (15 min, 4° C.).

The supernatant was added to 4 ml of a 50% slurry of glutathione-Sepharose 4B beads in lysis buffer and incubated for 4 h at 4° C. with shaking. The slurry was poured into a disposable Econo-Pac chromatography column from Bio-Rad (Hercules, Calif., USA) and washed 5 times with 10 bed volumes of lysis buffer. For cleavage of the fusion proteins from glutathione S-transferase, the beads were incubated with 5 U.S. National Institutes of Health (NIH) units thrombin (12 h, 4° C.). Thereafter, the protein was eluted with 12 ml lysis buffer. Thrombin was removed by precipitation with benzamidine-Sepharose beads (Amersham Pharmacia Biosciences, Piscataway, N.J., USA). After centrifugation at 500 g (10 min, room temperature), the buffer of the supernatant was exchanged to 20 mM HEPES (pH 7.5) using PD-10 columns, sterile filtered (0.22 µm), and used for cell culture experiments as indicated.

EXAMPLE 2

Synthesis of Recombinant C3Bot Polypeptides

C3bot$^{156}$-181 (SEQ ID No: 1), C3bot$^{163-177}$ (SEQ ID No: 11) and C3bot$^{154-182}$ (SEQ ID No: 18) were synthesized at IPF PharmaCeuticals GmbH (Hannover, Germany). The lyophilized polypeptides were reconstituted in 20 mM HEPES (pH 7.5), sterile filtered (0.22 µm), and used for cell culture experiments as indicated.

EXAMPLE 3

Cell Culture

Cells were prepared from fetal NMRI mice at embryonic day 16 (E16). Briefly dissected peaces of hippocampi were rinsed twice with phosphate-buffered saline (PBS), then with dissociation medium [modified essential medium (MEM) supplemented with 10% fetal calf serum, 100 IE Insulin/L, 0.5 mM glutamine, 100 U/ml penicillin/streptomycin, 44 mM glucose and 10 mM HEPES buffer] and dissociated mechanically. The suspension was centrifuged at 210 g for 2 min at 21° C., redissociated in starter medium (serum-free neurobasal medium supplemented with B27, 0.5 mM glutamine, 100 U/ml penicillin/streptomycin and 25 µM glutamate) and plated at a density of $2 \times 10^4$ cells/well on glass coverslips pre-coated with 0.5% poly-L-lysine followed by 40 mg/mL collagen dissolved in PBS layered in 24-multiwells. All ingredients were obtained from Gibco/BRL Life Technologies (Eggenstein, Germany).

Neurones were cultivated up to 14 days in-vitro (DIV) in a humidified atmosphere with 10% $CO_2$. One day after plating (DIV 1), C3bot$^{wt}$ full-length protein or polypeptide fragments (C3bot$^{154-182}$, C3bot$^{156-181}$, C3bot$^{163-177}$) were added to the culture medium at the indicated concentrations. Four days later (DIV 5), neurones were fixed.

EXAMPLE 4

Antibody Staining

Cells were fixed with 4% formaldehyde for 15 min and subsequently permeabilized for 30 min at room temperature using 0.3% Triton X-100 dissolved in PBS. Neurones were stained with primary antibodies overnight at 4° C. After washing in PBS, secondary antibodies were applied for 1 h at room temperature.

Hippocampal neurones were stained by a monoclonal antibody against neurofilament protein (NFP; 200 kDa, final dilution 1:200) and a polyclonal antiserum against microtubule associated proteins 2 (MAP2, final dilution 1:500), both from Chemicon International (Hofheim, Germany) to mark axons or dendrites, respectively. Synaptophysin-containing terminals were visualized using a monoclonal anti-synaptophysin (SyP) antibody (Progene GmbH, Heidelberg, Germany). Chicken anti-green fluorescent protein (GFP) antiserum was used to enhance enhanced GFP (eGFP) fluorescence (Invitrogene, Eugene, Oreg., USA).

Immunoreactivity was visualized using horse anti-mouse and goat anti-chicken coupled to Alexa 488 and goat anti-rabbit coupled to Alexa 594 (Molecular Probes, Eugene, Oreg., USA).

Neurones were morphometrically analysed as described below. Fluorescence was visualized either by using upright Leica DMLB epifluorescence equipment (Leica Microsystems, Wetzlar, Germany) or by confocal laser scanning microscopy.

For Image acquisition, a Leica TCS SL confocal laser Scanning microscope using an X40 oil-immersion objective was used. Fluorescent dyes were excited at a wavelength of 488 nm (green fluorescence) and 543 nm (red fluorescence), respectively. Fluorescence from green and red channels was collected sequentially using two Filters at 498-535 nm and 587-666 nm, respectively. Images were captured at a resolution of 1024×1024 pixels.

FIG. 1A shows a confocal image of a fixed hippocampal neuronal cell immunostained for neurofilament protein of 200 kDa (NFP, red) and microtubule-associated protein 2 (Map2, green) as axonal or dendritic marker, respectively. Mouse hippocampal cultures were prepared at embryonic day 16 (E16) and cultivated for 5 days (DIV 5) with no further additions. At this time point, neurones had developed a definite axon and several dendrites. The dendrites as well as the soma of the neurone show a green fluorescence, the axon shows a orange fluorescence (overlay of green and red) and the axon segments exhibit a red fluorescence. The green fluorescence is shown in white and the red fluorescence is shown in grey.

EXAMPLE 5

Morphometrical Analysis

Total length and overall number of branches from axons and dendrites were analysed morphometrically using the Neurolucida soft-ware (MicroBrightField, Williston, Vt., USA).

The parameter "axon length" represents the integral length of all visible parts of an axon, including its higher-order branches. A segment count of individual branches of defined order was also performed (see FIG. 1B). Axon segment orders are displayed as percentage of cells expressing axon branches (referred to as segments) of the respective order. Counts were restricted up to the $10^{th}$ order.

The data displayed in a graph refer to a single representative experiment, if not mentioned otherwise. Experiments were carried out on the basis of cultures prepared on the same day, from the same animal pool. Typically, 3 coverslips were prepared per condition, and 10 neurones were evaluated on each coverslip. Provided no significant differences between coverslip means (tested by ANOVA), data were pooled and given as means±SE. Experiments were repeated at least 3 times following identical experimental protocols. Effects of C3bot$^{wt}$ and of C3-derived polypeptide fragments (C3bot$^{154-182}$, C3bot$^{156-181}$, C3bot$^{163-177}$) were statistically analysed using Student's t test on the basis of a significance level of 0.05.

FIG. 1B shows a simplified drawing of FIG. 1A used for segment order analysis. Segment order analysis of axonal branching was performed as show above. Axon trunk extending from cell body is first-Order segment. Branches emerging from first bifurcation represent second-Order segments, branches extending from a bifurcation of a second-Order segment represent third-Order segments, and so on. The axon shown in FIG. 1B exhibit up to $9^{th}$ order segments.

EXAMPLE 6

ADP-Ribosylation of RhoA

Figure 2:
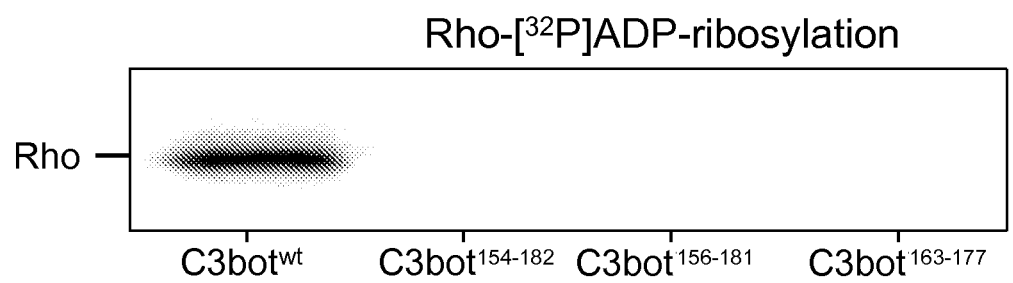

ADP ribosylation of RhoA from rat brain lysate (50 μg) was performed using 5 μM $C3bot^{wt}$, $C3bot^{154-182}$, $C3bot^{156-181}$ and $C3bot^{163-177}$ in the presence of 1 μM [$^{32}$P] NAD for 15 min at 37° C. Samples were subjected to SDS-PAGE followed by autoradiography. FIG. 2 shows the results.

A strong band is detected after incubation with the $C3bot^{wt}$ protein showing the functional ribosylation activity. All polypeptides fail to transfer the radioactive substrate to the RhoA protein so that no band occurred. Thus, $C3bot^{156-181}$ and $C3bot^{163-177}$ polypeptide do not perform ADP-ribosylation of RhoA.

EXAMPLE 7

RalA Interaction with $C3Bot^{wt}$ and C3Bot Polypeptide Fragments

Rat brain lysate (50 μg) was incubated with RalA (5 μM) in the presence or absence of the polypeptides ($C3bot^{154-182}$ (lanes 3, 6 and 9), $C3bot^{166-181}$ (lanes 4, 7 and 10) and $C3bot^{163-177}$ (lanes 5, 8 and 11); 400 μM each) for 30 min at 4° C. ADP-ribosylation of RhoA (from rat brain lysate) was then performed using 50 nM $C3bot^{wt}$ in the presence of 1 μM [$^{32}$P]NAD for 10 min at 37° C. Samples were subjected to SDS-PAGE followed by autoradiography.

Experimental set-up is based on the following competitive system. If RalA interacts with the $C3bot^{wt}$ a reduced ADP-ribosylation signal of RhoA should be detected. If RalA is bound to another binding partner, it cannot interact with $C3bot^{wt}$ anymore and the signal of ADP-ribosylation of RhoA should increase until maximal level.

FIG. 3 shows the results.

In the absence of RalA $C3bot^{wt}$ shows its normal RhoA-ADP-ribosylation activity. As expected a strong band occurred which is used as negative control (lane 1, 12). If RalA binds to $C3bot^{wt}$ it inhibits $C3bot^{wt}$-catalyzed RhoA-[$^{32}$P]ADP ribosylation so that the resulting radioactive signal is much weaker (lane 2, positive control, i.e. interaction of $C3bot^{wt}$ and RalA). The addition of $C3bot^{154-182}$, $C3bot^{156-181}$ and $C3bot^{163-177}$ polypeptides alone does not alter the ADP-ribosylation activity of $C3bot^{wt}$ (strong band at lanes 3-5). Lanes 6-8 show the results after incubation with the polypeptides and RalA. The achieved signal is as weak as the signal achieved with RalA alone (lane 2). Thus, the $C3bot^{154-182}$, $C3bot^{156-181}$ and $C3bot^{163-177}$ polypeptides do not interact with RalA, so that the polypeptides were not able to abrogate the effect of RalA. Heat-denatured RalA, which was also applied as negative control, had no effect on the ADP ribosylation activity of $C3bot^{wt}$ as expected (strong band, lanes 9-11).

EXAMPLE 8

Transiently Activation of RhoA

J774A.1 cells (ECACC 91051511) were lysed in lysis buffer (50 mM Tris, pH 7.2; 150 mM NaCl; 5 mM $MgCl_2$; 1% Nonidet P-40; 1 mM phenylmethanesulfonyl fluoride; 5 mM dithiothreitol; and protease inhibitor cocktail, EDTA free). Cell lysates were then incubated with $C3bot^{154-182}$, $C3bot^{156-181}$ or $C3bot^{163-177}$ (5 μM each) at 30° C.

After 0, 5, 15 and 30 minutes the level of active RhoA (RhoA-GTP) was determined using the Rhotekin pull-down assay.

For Rhotekin pull-down assay the Rho binding domain C21 (kind gift of Dr. John Collard, The Netherlands Cancer Institute, Amsterdam, The Netherlands), encoding the N-terminal 90 amino acids of Rhotekin, was expressed as GST-fusion protein in *E. coli* and purified by affinity chromatography using glutathione-sepharose.

Cell lysates of J774A.1 cells incubated for different time periods with the C3bot polypeptide fragments ($C3bot^{154-182}$, $C3bot^{156-181}$ or $C3bot^{163-177}$, 5 μM each) were then added to glutathione-bound GST-C21 (Rhotekin) for 1 h (4° C.). The beads were washed 3 times, and bound proteins were mobilized by incubation with Laemmli sample buffer at 95° C. for 10 min. Samples were submitted to SDS-PAGE and Western blot analysis. For immunoblotting a mouse monoclonal immunoglobulin G (IgG) from Santa Cruz Biotechnologies (Santa Cruz, Calif., USA) was used to detect RhoA. Detection was performed using horseradish peroxidase conjugated secondary antibody (mouse, Rockland Immunochemicals, Inc.). For the chemoluminescence reaction, ECL Femto (Pierce, Part of Thermo Fisher Scientific, Inc.) was used.

FIG. 4 shows the results of the influence of C3bot polypeptide fragments ($C3bot^{154-182}$, $C3bot^{156-181}$ and $C3bot^{163-177}$ to RhoA activity. After incubation of J774A.1 with $C3bot^{154-182}$ the level of GTP-bound RhoA was not altered over 15 min. $C3bot^{154-182}$ was used as control polypeptide of the prior art. In contrast after incubation with $C3bot^{156}$-181 and $C3bot^{163-177}$ the levels of GTP-bound RhoA were increased after 5 min. After 15 min the level of GTP-bound RhoA was comparable to that of untreated cells. After 30 min, the level of GTP-bound RhoA was reduced by all three polypeptides ($C3bot^{154-182}$, $C3bot^{156-181}$ and $C3bot^{163-177}$) compared to untreated cells. In summary, $C3bot^{154-182}$ decreased the level of GTP-bound RhoA over time. In contrast, $C3bot^{156-181}$ and $C3bot^{163-177}$ are able to induce a transient RhoA activation in J774A.1 cells, which is followed by a moderate inactivation which results in a complete inactivation. After the triggered activation by $C3bot^{156-181}$ or $C3bot^{163-177}$ the level of GTP-bound RhoA is 2-3 fold higher than that observed after incubation with the $C3bot^{154-182}$. The induction of a short RhoA activation peak mimics the physiological conditions, i.e. a RhoA activation/inactivation cycle.

EXAMPLE 9

Figure 5:
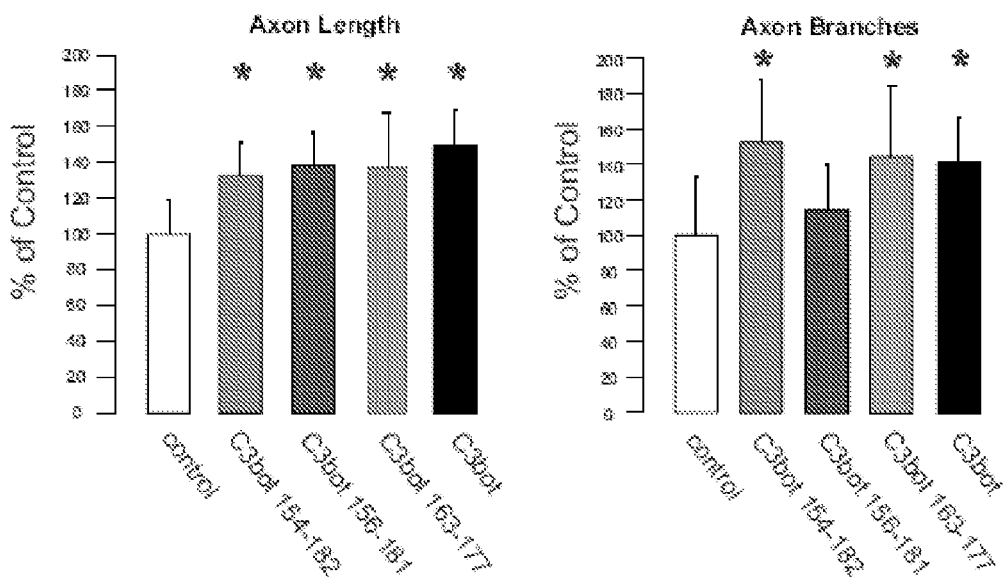
Figure 5:
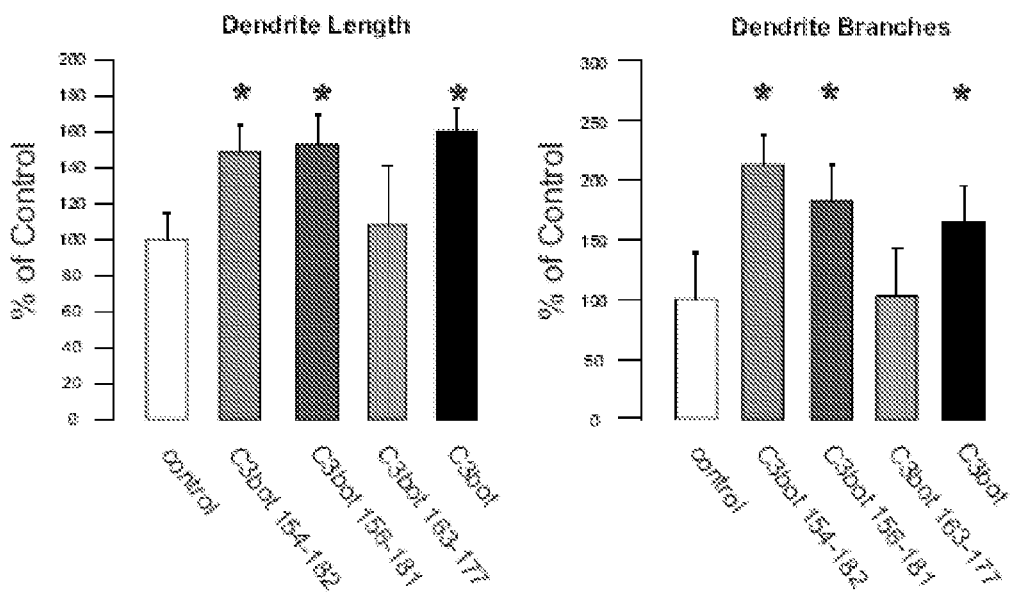
Figure 6:
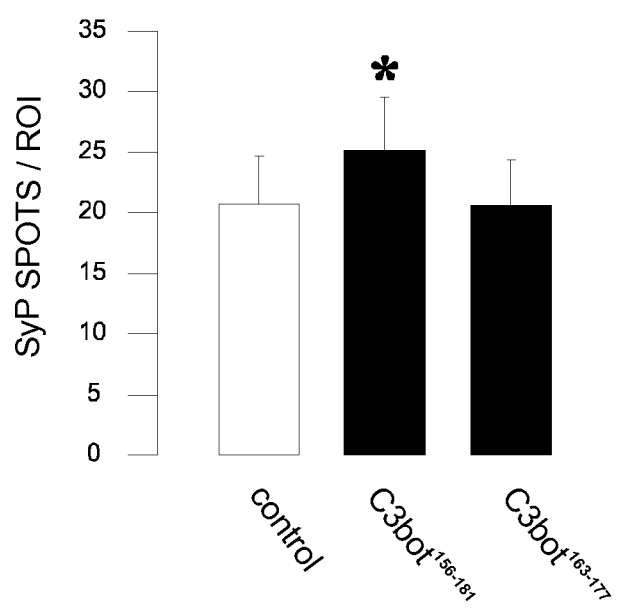
Figure 7:
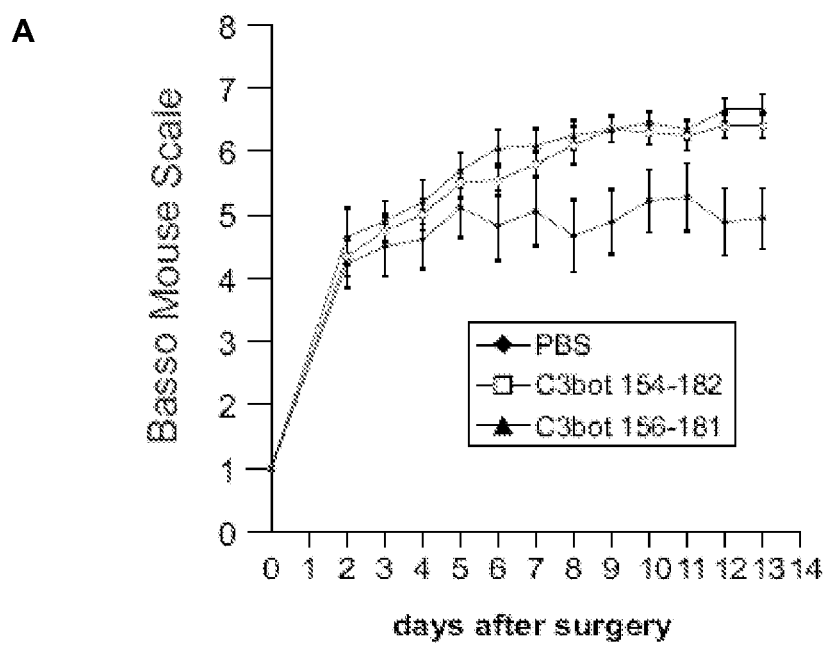
Figure 7:
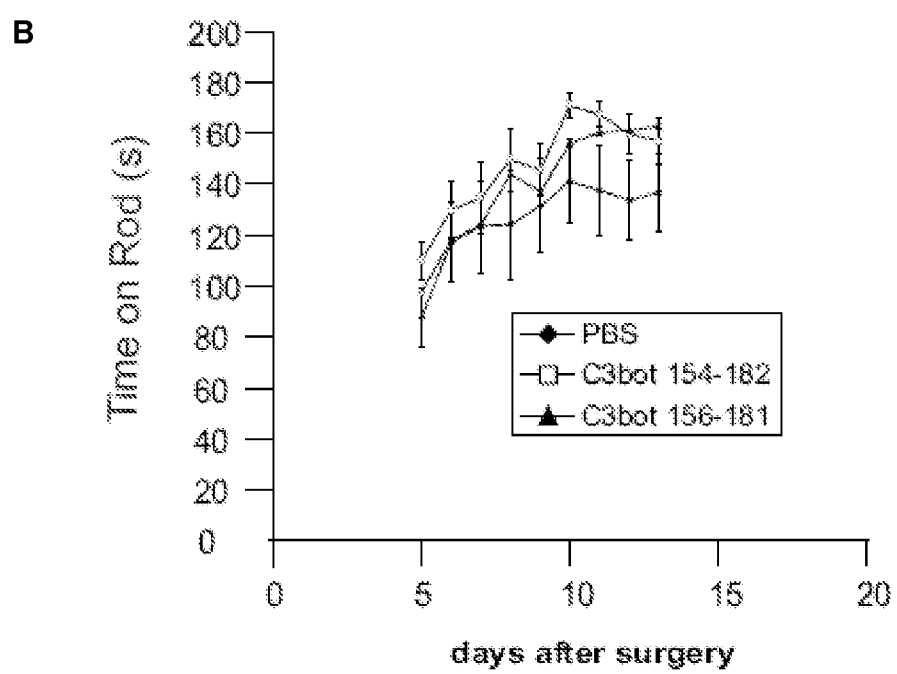

Effects of C3Bot Polypeptide Fragments on Process Growth of Hippocampal Neurones Mouse hippocampal cultures were prepared as shown in example 3 at embryonic day 16 (E16) and cultivated for five days (DIV 5). Cells were incubated either with $C3bot^{wt}$ (80 nM) or C3bot polypeptide fragments ($C3bot^{154-182}$, $C3bot^{156-181}$ or $C3bot^{163-177}$, 50 nM each). $C3bot^{154-182}$ was used as comparative polypeptide of the state of the art. After four days of incubation cells were fixed and immunostained for neurofilament protein of 200 kDa (NFP) and microtubule associated protein 2 (Map2) as axonal or dendritic marker, respectively according to example 4. At this time point, neurones had developed a definite axon and several dendrites. Total length and the overall number of branches from axons and dendrites were analyzed morphometrically as shown in example 5. FIG. 5 shows the results.

FIG. 5A shows the effect of the polypeptides to axonal length and branching. Hippocampal neurones under control conditions developed axonal branches up to the $8^{th}$ order. The C3bot$^{wt}$ and the C3bot polypeptide fragments (C3bot$^{154-182}$, C3bot$^{156-181}$ and C3bot$^{163-177}$) significantly enhanced the formation of middle to higher order branches. Branches of up to the $10^{th}$-segment order were observed. Further the overall axon length was significantly enhanced. Application of each of the three polypeptides resulted in axon elongation comparable to the effects elicited by C3bot$^{wt}$. The effects of the polypeptides of the invention (C3bot$^{156-181}$ and C3bot$^{163-177}$) were slightly greater than that achieved with the control polypeptide (C3bot$^{154-182}$). Axon branching was also increased by the polypeptides and C3bot$^{wt}$ comparably, but the effects for C3bot$^{156-181}$ were less pronounced.

In FIG. 5B the effects of dendritic length and branching are shown. C3bot$^{154-182}$ and C3bot$^{156-181}$ polypeptides increase the length and the branching of dendrites significantly. In general the effects are comparable to that achieved with the C3bot$^{wt}$. With respect to dendrite branching the effect achieved with both polypeptides (C3bot$^{154-182}$ and C3bot$^{156-181}$) is better than that achieved with the wild type protein. Only C3bot$^{163-177}$ does not show any effect on either parameter. Dendrites are not influenced by said polypeptide.

In summary, the C3bot$^{156-181}$ polypeptide shows comparable axon- and dendritic promoting effects in cultivated hippocampal neurones. The C3bot$^{163-177}$ polypeptide exhibits selective axonotropic effects not involving dendritic stimulation.

EXAMPLE 10

$C3Bot^{156-181}$ but not $C3Bot^{163-177}$ Affects the Number of Synaptophysin (SyP) Expressing Synaptic Terminals in Hippocampal Neurons Hippocampal neurons cultured at high density (75,000 $cm^2$) were incubated with 50 nM each of $C3bot^{156-181}$ and $C3bot^{163-177}$ from DIV 4-7. Control cells were incubated without a polypeptide. Cultures were transfected with eGFP to visualize nonoverlapping individual neurons using the Effectene transfection reagent (Quiagen, Hilden, Germany). After an expression period of 22 h, cultures were fixed and stained for eGFP (to further enhance green fluorescence) and synaptophysin (SyP). Labeled neurons were visualized by epifluorescence using an x63 oil immersion objective. Stained terminal were quantified within a circular region of interest (ROI) with a diameter of 100 μm centered on the somata of individual transfected neurons. The number of contacting SyP spots on eGFP expressing dendrites was calculated using the in-house written software NeMo. FIG. 6 shows the results. Incubation with $C3bot^{156-181}$ increases the number of contacting SyP spots up to 20%. Application of $C3bot^{163-177}$ does not alter the number of SyP terminals.

EXAMPLE 11

Effects of C3Bot Polypeptides on Behavioural Recovery after Spinal Cord Injury Adult anesthetized mice received laminectomy followed by contusive spinal cord lesion at thoracic segment Th8. Immediately after injuring the dura was perforated and 5 μl of the $C3bot^{156-181}$ polypeptide and the $C3bot^{154-182}$ polypeptide (40 μM each) were administered by placing a permanent piece of gel-foam at the site of lesion. Control animals received PBS treatment only, $C3bot^{154-182}$ was used as control polypeptide of the prior art. After surgical dressing animals were left to recover. Functional recovery was followed by two behavioural test.

Starting two days after surgery an established open field behavioural test for locomotor activity (Basso Mouse Scale for Locomotion, BMS) was used to follow functional recovery of the animals within 2 post-surgical weeks. The test was performed according to Basso D M et al., J. Neurotrauma, May 1, 2006, 23(5): 635-659. FIG. 7A shows the results.

Treated animals performed better than control animals during the entire time course. The results achieved with the $C3bot^{156-181}$ polypeptide of the invention are slightly better than the results achieved with the control polypeptide $C3bot^{154-182}$. The positive effects were achieved applying only a single dose. At the end of the observation period peptide treated animals ended up with a locomotor score of ~6.5, whereas control animals only reached a score of 5.

A second established behavioural test was applied in which the time was measured the mice stayed on a rotating rod (Rotarod). The maximal time on rod is 180 sec. During this observation period speed increases constantly.

FIG. 7B shows the results.

The treadmill test was started 5 days after surgery. Especially during the last week of the observation period, the performance of mice that received either of the polypeptides ($C3bot^{154-182}$, $C3bot^{156-181}$) improved significantly compared to the control animals. The performance of mice treated with the polypeptide of the invention ($C3bot^{156-181}$) showed a smaller effect at the beginning, but a better effect was achieved at the end of the experiment compared to the polypeptide of the state of the art ($C3bot^{154-182}$).

In summary, it was shown that the C3bot-derived polypeptides of the invention foster functional recovery after contusive spinal cord injury in the in-vivo mouse model. Compared to a polypeptide of the state art slightly better results could be achieved.

The invention claimed is:

1. A polypeptide:
   a) consisting of the amino acid sequence selected from the group consisting of: SEQ ID No: 1 to SEQ ID No: 16, or
   b) comprising at least two identical amino acid sequences selected from a),
   wherein the polypeptide of a) or b) activates Ras homolog gene family member A (RhoA) GTPase.

2. The polypeptide of claim 1, wherein the polypeptide consists of the amino acid sequence selected from the group consisting of SEQ ID No: 1 to SEQ ID No. 10, and its modifications according to b).

3. The polypeptide of claim 2 which consists of the amino acid sequence of SEQ ID No. 1.

4. The polypeptide of claim 1, wherein the polypeptide consists of the amino acid sequence selected from the group consisting of SEQ ID No: 11 to SEQ ID No: 16, and its modifications according to b).

5. The polypeptide of claim 4 which consists of the amino acid sequence of SEQ ID No. 11.

6. The polypeptide of claim 1, bound to or encapsulated into a transport agent facilitating the uptake of the polypeptide into mammalian cells.

7. A polynucleotide consisting of a nucleotide sequence encoding the polypeptide of claim 1, wherein the polynucleotide is genomic DNA, cDNA or RNA.

8. A vector comprising said polynucleotide of claim 7.

9. A host cell transfected with said vector of claim 8.

10. A pharmaceutical composition comprising a pharmaceutically effective amount of the polypeptide of claim 1, and further comprising a pharmaceutically acceptable excipient.

11. A method for alleviating damage of the central or peripheral nervous system in a mammal comprising administering to a mammal in need thereof an effective amount of at least one polypeptide consisting of the amino acid sequence selected from the group consisting of SEQ ID No: 1 to SEQ ID No: 16 or identical repeats of said polypeptide, or a pharmaceutical composition thereof.

12. The method according to claim 11 wherein the at least one polypeptide consists of an amino acid sequence selected from the group consisting of SEQ ID No: 11 to SEQ ID No: 16 or identical repeats of said polypeptide, or a pharmaceutical composition thereof.

13. A kit comprising the polypeptide of claim 1, or a pharmaceutical composition thereof, and optionally comprising written instructions for use and/or means for administration.

* * * * *

UNITED STATES PATENT AND TRADEMARK OFFICE
CERTIFICATE OF CORRECTION

PATENT NO. : 8,747,841 B2  
APPLICATION NO. : 13/262607  
DATED : June 10, 2014  
INVENTOR(S) : Ahnert-Hilger et al.

Page 1 of 1

It is certified that error appears in the above-identified patent and that said Letters Patent is hereby corrected as shown below:

On the title page item (73), corrections to read:

Assignees: Ingo Just

Gudrun Ahnert-Hilger

Markus Holtje

Signed and Sealed this  
First Day of September, 2015

Michelle K. Lee  
*Director of the United States Patent and Trademark Office*

SEQUENCE LISTING

```
<160> NUMBER OF SEQ ID NOS: 18

<210> SEQ ID NO 1
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1
```

```
Lys Gly Ser Lys Ala Gly Tyr Ile Asp Pro Ile Ser Ala Phe Ala Gly
1               5                   10                  15

Gln Leu Glu Met Leu Leu Pro Arg His Ser
            20                  25

<210> SEQ ID NO 2
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Ser Lys Ala Gly Tyr Ile Asp Pro Ile Ser Ala Phe Ala Gly Gln
1               5                   10                  15

Leu Glu Met Leu Leu Pro Arg His Ser
            20                  25

<210> SEQ ID NO 3
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Gly Ser Lys Ala Gly Tyr Ile Asp Pro Ile Ser Ala Phe Ala Gly
1               5                   10                  15

Gln Leu Glu Met Leu Leu Pro Arg His
            20                  25

<210> SEQ ID NO 4
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ser Lys Ala Gly Tyr Ile Asp Pro Ile Ser Ala Phe Ala Gly Gln Leu
1               5                   10                  15

Glu Met Leu Leu Pro Arg His Ser
            20

<210> SEQ ID NO 5
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Lys Gly Ser Lys Ala Gly Tyr Ile Asp Pro Ile Ser Ala Phe Ala Gly
1               5                   10                  15

Gln Leu Glu Met Leu Leu Pro Arg
            20

<210> SEQ ID NO 6
<211> LENGTH: 24
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 6

Gly Ser Lys Ala Gly Tyr Ile Asp Pro Ile Ser Ala Phe Ala Gly Gln
1               5                   10                  15

Leu Glu Met Leu Leu Pro Arg His
            20

<210> SEQ ID NO 7
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Lys Ala Gly Tyr Ile Asp Pro Ile Ser Ala Phe Ala Gly Gln Leu Glu
1               5                   10                  15

Met Leu Leu Pro Arg His Ser
            20

<210> SEQ ID NO 8
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ser Lys Ala Gly Tyr Ile Asp Pro Ile Ser Ala Phe Ala Gly Gln Leu
1               5                   10                  15

Glu Met Leu Leu Pro Arg His
            20

<210> SEQ ID NO 9
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Ser Lys Ala Gly Tyr Ile Asp Pro Ile Ser Ala Phe Ala Gly Gln
1               5                   10                  15

Leu Glu Met Leu Leu Pro Arg
            20

<210> SEQ ID NO 10
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Lys Gly Ser Lys Ala Gly Tyr Ile Asp Pro Ile Ser Ala Phe Ala Gly
1               5                   10                  15

Gln Leu Glu Met Leu Leu Pro
            20
```

-continued

```
<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ile Asp Pro Ile Ser Ala Phe Ala Gly Gln Leu Glu Met Leu Leu
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Tyr Ile Asp Pro Ile Ser Ala Phe Ala Gly Gln Leu Glu Met Leu Leu
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ile Asp Pro Ile Ser Ala Phe Ala Gly Gln Leu Glu Met Leu Leu Pro
1               5                   10                  15

<210> SEQ ID NO 14
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ile Asp Pro Ile Ser Ala Phe Ala Gly Gln Leu Glu Met Leu Leu Pro
1               5                   10                  15

Arg

<210> SEQ ID NO 15
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Tyr Ile Asp Pro Ile Ser Ala Phe Ala Gly Gln Leu Glu Met Leu Leu
1               5                   10                  15

Pro

<210> SEQ ID NO 16
<211> LENGTH: 17
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 16

Gly Tyr Ile Asp Pro Ile Ser Ala Phe Ala Gly Gln Leu Glu Met Leu
1               5                   10                  15

Leu

<210> SEQ ID NO 17
<211> LENGTH: 211
<212> TYPE: PRT
<213> ORGANISM: Clostridium botulinum

<400> SEQUENCE: 17

Ala Tyr Ser Asn Thr Tyr Gln Glu Phe Thr Asn Ile Asp Gln Ala Lys
1               5                   10                  15

Ala Trp Gly Asn Ala Gln Tyr Lys Lys Tyr Gly Leu Ser Lys Ser Glu
            20                  25                  30

Lys Glu Ala Ile Val Ser Tyr Thr Lys Ser Ala Ser Glu Ile Asn Gly
        35                  40                  45

Lys Leu Arg Gln Asn Lys Gly Val Ile Asn Gly Phe Pro Ser Asn Leu
    50                  55                  60

Ile Lys Gln Val Glu Leu Asp Lys Ser Phe Asn Lys Met Lys Thr
65                  70                  75                  80

Pro Glu Asn Ile Met Leu Phe Arg Gly Asp Asp Pro Ala Tyr Leu Gly
                85                  90                  95

Thr Glu Phe Gln Asn Thr Leu Leu Asn Ser Asn Gly Thr Ile Asn Lys
            100                 105                 110

Thr Ala Phe Glu Lys Ala Lys Ala Lys Phe Leu Asn Lys Asp Arg Leu
        115                 120                 125

Glu Tyr Gly Tyr Ile Ser Thr Ser Leu Met Asn Val Ser Gln Phe Ala
    130                 135                 140

Gly Arg Pro Ile Ile Thr Lys Phe Lys Val Ala Lys Gly Ser Lys Ala
145                 150                 155                 160

Gly Tyr Ile Asp Pro Ile Ser Ala Phe Ala Gly Gln Leu Glu Met Leu
                165                 170                 175

Leu Pro Arg His Ser Thr Tyr His Ile Asp Asp Met Arg Leu Ser Ser
            180                 185                 190

Asp Gly Lys Gln Ile Ile Ile Thr Ala Thr Met Met Gly Thr Ala Ile
        195                 200                 205

Asn Pro Lys
    210

<210> SEQ ID NO 18
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Val Ala Lys Gly Ser Lys Ala Gly Tyr Ile Asp Pro Ile Ser Ala Phe
1               5                   10                  15

Ala Gly Gln Leu Glu Met Leu Leu Pro Arg His Ser Thr
            20                  25